United States Patent [19]

Kamenka et al.

[11] Patent Number: 5,972,952
[45] Date of Patent: Oct. 26, 1999

[54] NEUROPROTECTIVE PHARMACEUTICAL COMPOSITION CONTAINING STEREOISOMERS OF ARYLCYCLOHEXYLAMINES

[75] Inventors: Jean-Marc Kamenka; Martine Michaud; Marie-Jeanne Drian; Jacques Vignon, all of Montpellier; Alain Privat, Saint-Clement de Riviere, all of France

[73] Assignee: Le Centre National De La Recherche Scientifique, Paris, France

[21] Appl. No.: 08/762,925

[22] Filed: Dec. 10, 1996

Related U.S. Application Data

[60] Provisional application No. 60/011,753, Dec. 11, 1995.

[51] Int. Cl.[6] .............................. A01N 43/42; A01N 43/40
[52] U.S. Cl. ............................. 514/279; 514/315
[58] Field of Search .................................... 514/315, 277, 514/279, 280, 284, 285, 327, 319

[56] References Cited

U.S. PATENT DOCUMENTS

| | | | |
|---|---|---|---|
| 2,921,076 | 1/1960 | Parcell | 546/213 |
| 3,192,219 | 6/1965 | Maddox et al. | 546/192 |
| 5,132,313 | 7/1992 | Kozikowski et al. | 514/325 |
| 5,179,109 | 1/1993 | Kamenka et al. | 514/326 |

OTHER PUBLICATIONS

Michaud et al. Eur. J. Med. Chem. (1994) 29: 869–876.
Chadwick et al., J.C.S. Perkin I 887–893, 1977.
Chaudieu et al., "Role of the Aromatic Group in the Inhibition of Phencyclidine Binding and Dopamine Uptake By PCP Analogs", Pharmacology Biochemistry & Behavior 32:699–705, 1989.
Drian et al., "Non–Competitive Antagonists of N–Methyl–D–Aspartate Prevent Spontaneous Neuronal Death in Primary Cultures of Embryonic Rat Cortex", J. of Neuroscience Research 29:133–138, 1991.
Ilagouma et al., "Arylcyclohexylamines Derived from BTCP are Potent Indirect Catecholamine Agonists", Eur. J. Med. Chem 28:377–385, 1993.
Iorio et al., J. Med. Chem. 34:2615–2623, 1991.
Levallois et al., "TCP Enhances the Survival of Human Fetal Spinal Cord Cells in Culture", Brain Research 573:327–330, 1992.
Lockhart et al., Brain Research 630:32–40, 1993.
Rondouin et al., Neuroscience Letters 91:199–203, 1988.
Thurkauf et al., "Synthesis, Pharmacological Action, and Receptor Binding Affinity of the Enantiomeric 1–(1–Phenyl–3–methylcyclohexyl)piperidines", J. Med. Chem. 31:1625–1628, 1988.
Vignon et al., "Sigma and Phencylidine–Like Compounds as Molecular Probes in Biology," Domino Ed. pp. 199–208, 1988. (NFF Books: Ann Arbor, MI
Vincent et al., "Interaction of Phencyclidine ("angel dust") with a Specific Receptor in Rat Brain Membranes" Proc. Natl. Acad. Sci. 76:4678–4682, 1979.

*Primary Examiner*—Jon P. Weber
*Assistant Examiner*—Susan Hanley
*Attorney, Agent, or Firm*—John D. Conway; William McGowan; Fish & Richardson

[57] ABSTRACT

The invention relates to pharmaceutical compositions for neuroprotection containing the compound (1S,2R) 1-[1-(2-thienyl)-2-alkylcyclohexyl]piperidine or (1S,2R) 1-[1-(2-furanyl)-2-alkylcyclohexyl]piperdine, or their pharmaceutically acceptable salts. The synthesis and method separation of racemic mixtures to provide pure enantiomers is presented. The compositions have use in the treatment of stroke, CNS trauma and Alzheimer's disease.

20 Claims, No Drawings

NEUROPROTECTIVE PHARMACEUTICAL COMPOSITION CONTAINING STEREOISOMERS OF ARYLCYCLOHEXYLAMINES

BACKGROUND OF THE INVENTION

Under 35 USC §119(e)(1), this application claims the benefit of prior U.S. provisional application Ser. No. 60/011,753, filed Dec. 11, 1995.

BACKGROUND OF THE INVENTION

Excitatory amino acids (EAA), such as L-glutamate and L-aspartate, are involved in both excitatory neurotransmission and synaptic plasticity in the central nervous system (CNS). Lockhart, et al., Brain Res. 630:32–40 (1993). EAAs, however, are also neurotoxic and have been believed to be involved in an important mechanism associated with neuronal injury and death. Indeed, EAAs have been implicated in both acute traumatic events, such as stroke-induced hypoxia or ischemia, and chronic neuro-degenerative diseases, such as Huntington's Chorea and Alzheimer's disease. Farougui, et al., Brain Res. Rev. 16:171–191 (1991).

The agonist-induced overactivation of the N-methyl-D-asparate (NMDA) receptor by EAAs is believed to be the principal factor underlying the neurotoxic effect. The activation of the NMDA receptor by EAAs induces an influx of sodium and calcium ions into the cells, which results in neuronal death. Choi, et al., J. Neurosci. 7:369–379 (1987).

SUMMARY OF THE INVENTION

In one aspect, the present invention relates to a pharmaceutical composition containing the compound (1S,2R) 1-[1-(2-thienyl)-2-alkylcyclohexyl]piperidine or (1S,2R) 1 [1-(2-furanyl)-2-methylcyclohexyl]piperdine, or a pharmaceutically acceptable salt thereof.

The pharmaceutical compositions of the present invention contain (1) one or more of the compounds described above; (2) one or more pharmaceutically acceptable carriers, and, optionally; (3) one or more other ingredients such as another bioactive compound or stabilizing agent.

Both the compounds 1-[1-(2-thienyl)-2-alkylcyclohexyl]piperidine and 1-[1-(2-furanyl)-2-alkylcyclohexyl]piperidine have two asymmetric carbons, i.e., the carbon at position 1 and the carbon at position 2. Thus, there are four possible stereoisomers for each compound, i.e., (1S,2S), (1S,2R), (1R,2R), and (1R,2S). The present invention relates to a pharmaceutical composition containing at least one of the (1S,2R) stereoisomer compounds but not any of the (1S,2S), (1R,2R), or (1R,2S) stereoisomer compounds. The carrier must be "pharmaceutically acceptable" in the sense of being compatible with the compound(s) of the composition and not deleterious to the subject to be treated. The term "alkyl" refers to a linear or branched hydrocarbon having between one and six carbons, inclusive, e.g., methyl, ethyl, propyl, isopropyl, butyl, or t-butyl.

The compound contained within the pharmaceutical composition of this invention can be provided in the form of a pharmaceutically acceptable salt. Examples of such a salt include, but are not limited to, those formed with organic acids (e.g., acetic, lactic, maleic, citric, malic, fomaric, tartaric, salicylic, stearic, ascorbic, succinic, benzoic, methanesulfonic, toluenesulfonic, or pamoic acid), inorganic acids (e.g., hydrochloric, nitric, diphosphoric, sulfuric, or phosphoric acid), and polymeric acids (e.g., tannic acid, carboxymethyl cellulose, polylactic, polyglycolic, or copolymers of polylactic-glycolic acids).

The pharmaceutical composition may conveniently be presented in unit dosage form and may be prepared by any of the methods well known in the art of pharmacy. All methods include the step of bringing the compounds into association with a carrier which may contain one or more accessory ingredients. In general, the composition for pills, tablets, or capsules (e.g., for oral administration) or powders are prepared by uniformly and intimately blending the compounds with finely divided solid carriers, and then, if necessary as in the case of tablets, forming the product into the desired shape and size. The pill, tablet, or capsule can be coated with a substance capable of protecting the composition from the gastric acid or intestinal enzymes in the subject's stomach for a period of time sufficient to allow the composition to pass undigested into the subject's small intestine.

Compositions suitable for parenteral administration (e.g., subcutaneous, intravenous, or intermuscular), on the other hand, conveniently comprise sterile aqueous solutions of the compound(s) in water or saline to produce an aqueous solution, and rendering said solution sterile. The composition may be presented in unit or multi-dose containers, for example, sealed ampoules or vials.

In another aspect, the invention features a method of preventing neuronal death in a patient by administering to a patient a therapeutically effective amount of the pharmaceutical composition of the invention. The pharmaceutical composition of the invention can, for example, be used to treat: acute traumatic events such as stroke, CNS trauma (e.g., brain or spinal surgery or injury), injury resulting from neurotoxins, and epilepsy; chronic neurodegenerative diseases such as Huntington's Chorea, Alzheimer's disease, amyotrophic lateral sclerosis (ALS), AIDS-related neuronal degeneration, and brain aging; or other neurodegenerative disorders related to the overactivation of the NMDA receptor.

The amount of a pharmaceutical composition of the present invention for treating the above-mentioned diseases or disorders varies depending upon the manner of administration, the age and the body weight of the subject, and the condition of the subject to be treated, and ultimately will be decided by the attending physician. Such an amount of the pharmaceutical composition as determined by the attending physician is referred to herein as a "therapeutically effective amount".

Other features and advantages of the present invention will be apparent from the detailed description of the invention and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications mentioned herein are incorporated by reference.

Synthesis of cis (peperidine/methyl or pip/Me) 1-[1-(2thienyl)-2-methylcyclohexyl]-piperidine (a) 1-(RS)-(2-Thienyl)-2-(RS)-methylcyclohexan-1-ols The Grignard reagent resulting from the action of 8.25 g (0.05 M) of 2-bromothiophene on 2 g (0.08 M) ofmagnesium in the form of turnings is prepared in 75 ml of anhydrous ether. To it is added 5.6 g (0.05M) of 2-methylcyclohexanone dissolved in 75 ml of anhydrous ether. After stirring under reflux for 3 hours, the complex is decomposed by a cold, saturated $NH_4Cl$ solution and then, after settling, the liquids are extracted with ether (3×50 ml). After drying ($Na_2SO_4$) the ether was evaporated in vacuo to give 8.7 g (88.8%) of a mixture of epimeric alcohols (IR). The alcohols are not further purified as the following reaction takes place by carbocation.

(b) 1-(RS)-(2-Furanyl)-2-(RS)-methylcyclohexan-1-azides

At −5° C., preparation takes place of a suspension containing 6.5 g (0.1 M) of sodium azide, 82 g (0.5 M) of trichloroacetic acid and 100 ml of chloroform and vigorously stirred. To it is slowly added and dissolved in 70 ml of chloroform and at the same temperature, 8.7 g (0.045 M) of the previously obtained alcohols. Stirring and the temperature are maintained for 3 h (or until the alcohols disappear) which is followed by cold neutralization with $NH_4OH$, settling, extraction of the aqueous phase or chloroform (2×50 ml) and washing of the collected organic phases to a neutral pH value. After drying ($Na_2SO_4$) and vacuum evaporation, an oil residue is recovered, which weights 8.85 g and which essentially contains two unsaturated derivatives (highly minority) and two epimeric azides (IR) which, bearing in mind their relative instability, are not otherwise purified.

(c) cis and trans 1-(2-Thienyl)-2-methylcyclohexan-1-amines

The mixture of the two azides previously obtained from 8.85 g is dissolved in 100 ml of isopropanol and heated to 65° C. Portionwise addition takes place of Raney nickel (whilst maintaining the temperature) until the giving off of gas stops. This is followed by heating to 70° C. for 15 minutes, cooling to ambient temperature, filtering on celite, washing the latter with 100 ml of isopropanol, the addition of 200 ml of 20% HCl to the alcoholic phases and vacuum evaporation in order to eliminate the isopropanol. The cooled, residual aqueous phase is neutralized by $NH_4OH$. This is followed by the extraction with ether (3×50 ml), drying ($Na_2CO_3$) and evaporation of the solvent in vacuo to obtain 4.6 g of an oily residue, which essentially contains two epimeric primary amines (IR, GC/MS).

(d) cis (pip/Me) 1-[1-(2-Thienyl)-2-methylcyclohexyl] piperidine

The preceding amines (4.6 g) are dissolved in 100 ml of acetonitrile containing 5.2 g of 1,5-dibromopentane and 13 g of $K_2CO_3$. The highly stirred mixture is refluxed for 72 h and then cooled to ambient temperature. After filtering, addition takes place of 150 ml of 20% HCl, extraction with ether (2×50 ml) and the acid liquids, neutralized by $NH_4OH$ are in turn extracted with ether (3×50 ml). After drying ($Na_2CO_3$), the ethers are evaporated in vacuo to give 3.7 g of an oily residue essentially containing two isomeric tertiary amines (IR, GC/MS).

The mixture obtained is chromatographed on a high performance preparative chromatograph on silica in hexane, containing ether (95/5 v/v) to give a first clear oil fraction, which slowly crystallizes (40 to 41° C.) and which is analytically pure of 1.7 g of trans (pip/Me) 1-[1-(2thienyl)-2-methylcyclohexyl]piperidine; a second fraction of white crystals of 1.4 g (80 to 81° C.) which is analytically pure of cis (pip/Me) 1-[1-(2-thienyl)-2-methylcyclohexyl] piperidine and two other fractions representing 400 mg in all and constituted by primary amines which have not reacted and whose mixture is recyclable during a subsequent synthesis. By bubbling gaseous HCl into the ethereal solution of the crystallized bases, their solid white hydrochlorides are precipitated and, after recovery by suction filtering and vacuum drying, they melt respectively at 152 to 153° C. and 220 to 221° C. for the cis product HCl. The yield of the cis product base from the starting ketone is 10.5%. Therefore, the two stereoisomeric structures are easily differentiated by NMR of $^{13}C(CDCl_3)$ from the hydrochlorides (anancomeric conformations). In the product HCl, methyl, carbons $C_2$–$C_4$ and $C_6$ are more shielded than in the isomer with a lower melting point, as a result of the axial position of the methyl (instead of the equatorial position in the other isomer).

Synthesis of cis (pip/Me) 1-[1-(2-furanyl)-2-methylcyclohexyl]-piperidine (a) 1-(RS)-(2-Furanyl)-2-(RS)-methylcyclohexan-1-ols An n-butyl-Li (138 ml, 0.22 mol) solution (1.6 M in hexane) was added dropwise and slowly to a stirred solution of furan (15 g, 0.22 mol) and N,N,N',N'-tetramethylethylenediamine (TMEDA) (17.5 g, 0.15 mol) in anhydrous ether maintained between −10° C. and −5° C. under a nitrogen atmosphere. After this addition was completed, a 2-methylcyclohexanone (24.6 g, 0.22 mol) solution in ether (20 ml) was added dropwise, while the temperature was kept at −10° C. After the completion of the second addition, the solution was heated to 25° C. for 30 min. and then poured in a saturated solution of $NH_4Cl$. The aqueous solution was extracted with ether (3×100 ml), the organic layers dried over $MgSO_4$ and evaporated under reduced pressure to yield an oily residue (36.9 9). The raw alcohols were dissolved in ether, filtered on aluminoxide (Merck, Rahway, N.J., aluminum oxide 90) to yield, after evaporation under reduced pressure, a pure mixture of diastereoisomeric alcohols (33.9 g, 93%).

(b) 1-(RS)-(2-Furanyl)-2-(RS)-methylcyclohexan-1-azides

Trichloroacetic acid (49 9, 0.3 mol) dissolved in $CHCl_3$ (200 ml) was dropwise added to a stirred suspension of sodium azide (13 g, 0.2 mol) covered with $CHCl_3$. The solution was cooled to 12–13° C. and efficiently stirred until the medium resembled a jelly; the diastereoisomeric mixture of alcohols (20.4 g, 0.11 mol) was then dissolved in $CHCl_3$ (100 ml) and added dropwise. After the completion of the addition the medium was maintained at 12–13° C. and vigorously stirred for 3 days. A solution of ammonia 10% (200 ml) was then added and the aqueous phase extracted by $CH_2Cl_2$. The organic layer was then washed with water until neutrality, dried over $Na_2SO_4$, and evaporated under reduced pressure at room temperature until constant weight, to yield an oil residue (23.1 g) containing the diastereoisomeric azides used in the next step without further purification.

(c) cis and trans 1-(2-Furanyl)-2-methylcyclohexan-1-amines

The crude oily azide mixture (used as pure azide) (7.5 g, 0.037 mol) was dissolved in tetrahydrofuran (THF) (43 ml), and then triphenylphosphine (9.6 g, 0.037 mol) and water (1.6 g, 0.089 mol) were added. The mixture was left standing at room temperature under stirring for 3 days and was then heated at 35° C. for 3 h. After the reaction medium has been diluted with ether (160 ml), the organic layer was washed with water until neutrality, dried on $Na_2SO_4$, and evaporated under reduced pressure to yield a viscous oily residue. Petroleum ether was added to precipitate triphenylphosphine oxide. After filtration, the precipitate was rinsed with petroleum ether and the combined filtrates extracted with HCl 10% (3×50 ml). The acidic phase was neutralized with $NH_4OH$ 20%, extracted with ether (2×200 ml), dried over $MgSO_4$, and evaporated under reduced pressure to give a brownish oil (3.7 g) containing the crude diastereoisomeric primary amines. This oil was chromatographed on a preparative high performance liquid chromatography (HPLC) column (Modul Prep, Jobin-Yvon, filled with Merck silica gel 60). A mixture of petroleum ether, ether, and triethylamine (49.5:49.5:1 v/v) eluted first 1.9 g of pure cis amine (29% from alcohols), then 0.8 g of pure trans amine (12% from alcohols) both as colorless oils.

(d) cis (pip/Me) 1-[1-(2-Furanyl)-2-methylcyclohexyl] piperidine $K_2CO_3$ (3.6 g, 0.026 mol) and 1,5-dibromopentane (4.1 g, 0.018 mol) were added to a solution of the cis amine (1.9 g, 0.11 mol) in freshly distilled hexamethylphosphoramide (HMPA, Aldrich, St. Louis, Mo.) (21 ml). The reaction medium was heated to 50° C. and efficiently stirred for 4 days, and then poured in water (200 ml). The aqueous phase was extracted with petroleum ether (3×50 ml). The combined extracts were washed with HCl 10% (3×50 ml) and the aqueous phase neutralized ($NH_4OH$ 20%). The aqueous phase was submitted to extraction with ether (3×70 ml); the organic phase dried over $MgSO_4$, filtered over celite, and evaporated under reduced pressure to yield an oily residue (1.9 g) or crude product. Column chromatography (Chromagel 60–200, silica gel, Merck) in petroleum ether/ether (1:1 v/v) eluted pure product as a colorless oil (1.4 g, 54%). Hydrochlorination yielded a solid compound (mp 158–159° C.).

Optical Resolution of cis (pip/Me) 1-[1-(2-thienyl)-2-methylcyclohexyl]-piperidine (a) (1R,2S)1-[1-(2-Thienyl)-2-methylcyclohexyl]-piperidine (−)-Di-O,O'-4-toluoyltartaric acid (1.25 g, 3 mmol, $\alpha_D$=−136°) dissolved in minimum isopropanol (13 ml) was added in one portion to a cis (pip/Me) 1-[1-(2-thienyl)-2-methylcyclohexyl]-piperidine (1.7 g, 6.5 mmol) solution in minimum isopropanol (40 ml). The resulting solution was vigorously stirred at room temperature for 12 h, and then filtered to collect crystals, washed with isopropanol (30 ml) and petroleum ether (2×30 ml) to give 1.9 q salt. It was recrystallized 3 times in minimum isopropanol to yield 931.5 mg of the (−)-di-O,O'-4-toluoyltartaric acid salt of the product After regeneration of base form by neutralization ($Na_2CO_3$, 10%) followed by hydrochlorination, the HCl salt of the product (118 mg, 12%) was obtained (mp=221° C., $\alpha_D^{20}$=+31.9° (c=2, MeOH)). Injection of analytical samples of the product base onto a Chiralcel OD HPLC column, heated at 40° C., revealed a >99.5% enantiomeric purity ($R_T$=14.74 min). GC/MS analysis: $R_T$=19.11 min, m/e=263, purity >99%.

(b) (1S,2R)1-[1-(2-Thienyl)-2-methylcyclohexyl]-piperidine

All the above-obtained organic filtrates were pooled, evaporated under reduced pressure to dryness, and dissolved in ether (40 ml). After washing with $Na_2CO_3$ 10% (30 ml) and water (2×30 ml), and drying over $Na_2SO_4$, the organic phase was evaporated under reduced pressure to give a solid residue. This residue dissolved in isopropanol (40 ml) was treated with a unique addition of (+)-di-O,O'-4-toluoyltartaric acid (1.25 g, 3 mmol, $\alpha_D$=+136°) dissolved in minimum isopropanol (13 ml). After a work-up identical to (1R,2S) 1-[1-(2-thienyl)-2-methylcyclohexyl]-piperidine above, the product (115 mg, 12%) was obtained (mp=221° C., $\alpha_D^{20}$=−30.3° (c=2, MeOH)). HPLC analytical controls revealed a >99% enantiomeric purity ($R_T$=13.12 min), GC/MS analysis: $R_T$=19.11 min, m/e=263, purity >99%.

Optical Resolution of cis (Pip/Me) 1-[1-(2-furanyl)-2-methylcyclohexyll-piperidine (a) (1R, 2s) 1-[1-(2-Furanyl)-2-methylcyclohexyl]-piperidine (−)-di-O,O'-4-Toluoyltartaric acid (1.6 g, 3.8 mmol, $\alpha_{D=-}$136°) dissolved in minimum isopropanol (16 ml) was added in one portion to a solution of cis (pip/Me) 1-[1-(2-furanyl)-2-methylcyclohexyl]-piperidine (2.1 g, 8 mmol) dissolved in minimum isopropanol (49 ml). The resulting solution was treated as for (1R,2S)1-[1-(2-thienyl)-2-methylcyclohexyl]-piperidine (see above) to yield, after 3 recrystallizations in minimum isopropanol, 288 mg of (−)-diO-O'-4-toluoyltartaric acid salt of the product. After regeneration of the base form by neutralization ($Na_2CO_3$ 10%) followed by hydrochlorination, the HCl product (57 mg, 5%) was obtained (mp=158–159° C., $\alpha_D^{20}$=+31.4° (c−1.5 MeOH)). Injection of analytical samples of the product base onto a Chiralcel OD HPLC column revealed a 98% enantiomeric purity ($R_T$=10.92 min), GC/MS analysis: $R_T$=13.99 min, m/e=247, purity >99%.

(b) (1S,2R)1-[1-(2-Furanyl)-2-methylcyclohexyl]-piperidine

The filtrate obtained after the first filtration above was evaporated under reduced pressure to dryness and dissolved in ether (40 ml). After washing with $Na_2CO_3$ 10% (30 ml) and water (2×30 ml), and drying over $Na_2SO_4$, the organic phase was evaporated under reduced pressure to give a solid residue (1.078 g). This residue dissolved in isopropanol (29 ml) was treated by a unique addition of (+)-di-O-O'-4-toluoyltartaric acid (0.87 g, 2.2 mmol) dissolved in isopropanol (9.2 ml). After a work-up identical to that of (1R,2S) 1-[1-(2-furanyl)-2-methylcyclohexyl]-piperidine (see above), the HCl product (28 mg, 2.5%) was obtained (mp =158–159° C., $\alpha_D^{20}$=−34.35° (c−0.46, MeOH)). HPLC analytical controls revealed a >99.5% enantiomeric purity ($R_T$=10.15 min), GC/MS analysis: $R_T$=13.99 min, m/e=247, purity >99%.

Binding to the N-(1-phenylcyclohexyl)piperidine (PCP) Receptor

[$^3$H] 1-[1-(2-thienyl)-2-methylcyclohexyl]piperidine (TCP) binding to the PCP receptor was performed as previously described. Vignon, et al., Brain Research 280:194–197 (1983). The PCP receptor site is a regulatory site within the NMDA receptor complex. Scatton, B., Fundam. Clin. Pharmacol. 7:389 (1993) and J. T. Wroblewski, et al., Proc. Natl. Assoc. Sci. USA 89:5068 (1987). The rat brain (minus the cerebellum) was removed and homogenized with an Ultraturax (Ika Werke, Staufen, Germany, maximum setting) in a 50 mM Tris/HCl, pH 7.7 buffer for 20 s at 4° C. The homogenate was then centrifuged at 49,000 g for 20 min. and the pellet was resuspended in the same buffer and the homogenization-centrifugation steps performed a second time. The final pellet was resuspended in 10 volumes of a 50 mM Tris/Hepes, pH 7.7 buffer and used without further purification.

The homogenate (0.5–0.8 mg protein/ml) was incubated with N-[1-(2-thienyl) cyclohexyl]3,4-[$^3$H]piperidine ([$^3$H] TCP, 1 nM) (Amersham, Arlington Heights, Ill, 48 Ci/mmol) in a 5 mM Tris/Hepes, pH 7.7 buffer in the absence (total binding) and in the presence of the test compounds for 30 min. at 25° C. in a volume of 0.5 ml. The incubation was terminated by filtration over Whatman GF/B (Brandel, Gaithersberg, Md.) glass fiber filters presoaked in 0.05% polyethyleneimine (PEI, Aldrich, Milwaukee, Wis.) with an MR24 Brandel cell harvester (Brandel, Gaithersberg, Md.). The filters were rinsed twice with 5 ml of a 50 mM NaCl, Tris HCl 10 mM, pH 7.7 buffer and the radioactivity retained counted in 3.5 ml ACS (Amersham) with an Excel 1410 (LKB) liquid scintillation spectrophotometer. The nonspecific binding was determined in parallel experiments in the presence of 100 $\mu$M unlabeled TCP. The inhibition constants ($IC_{50}$) of the binding of [$^3$H]TCP for the two test compounds are presented in Table I. The $IC_{50}$ is the concentration of test compound required to inhibit 50 percent of specific binding. Thus, the test compounds are potent competitors in displacing [$^3$H]TCP from the PCP receptor site.

TABLE I

| TEST COMPOUND | IC$_{50}$ (nM) |
| --- | --- |
| (1S,2R) 1-[1-(2-thienyl)-2-methylcyclohexyl] piperidine | 4.3 ± 1.1 |
| (1S,2R) 1-[1-(2-furanyl)-2-methylcyclohexyl] piperidine | 5.5 ± 1.9 |

Protection of Cultured Neuronal Cells

Cultures of mixed neuronal and glial neocortical cells were prepared from 18-day-old Sprague-Dawley rat foetuses (IFFA-Credo, St. Germain l'Arbresle, France). The cerebral hemispheres were rapidly dissected in Hanks' BSS supplemented with glucose (6 g/l), incubated in trypsine-EDTA (5 min at 35° C.), rinsed with calcium/magnesium-free glucosed Hanks' and mechanically dissociated. After centrifugation (10 min, 70 g), the cells were resuspended in the culture medium consisting of 87% Eagle's minimal essential medium (MEM), 10% horse serum and 0.6% glucose (without antibiotics), and plated on poly-d-lysine (10 μg/cm$^2$) coated coverslips, in 24-well dishes, to a final density of 4×10$^5$ cells/cm$^2$ in 400 μl/well. The cultures were maintained for 2–3 weeks at 35° C. in a humidified atmosphere (95% air/5% CO$_2$), one-third of the medium being replaced every 4 days.

After 17–20 days in vitro, the culture medium was replaced with 400 μl of experimental medium (EM supplemented with glucose) containing the test compound for 5 min. at room temperature. This medium was replaced with the experimental medium containing the same concentration of test compound plus glutamate 500 μM for another 5 min. Finally, the cells were rinsed with the experimental medium and incubated for 24 h. The control cultures had received the same number of replacements of medium as the experimental ones, with standard experimental medium. The 100% neurotoxicity level was based on the effect of glutamate 500 μM for 5 min. The protective effect was quantified by estimation of the activity of the lactate dehydrogenase (LDH) released in the medium. Culture supernatant (100 μl) was added to phosphate buffer (875 μl, 125 mM, pH 7.6) containing 0.3 mM pyruvic acid and β-NADH (25 μl, 10 mg/ml). The decrease in absorbance was measured at 340 nm (Lockhart, et al., Brain Res. 630:36–40 (1993)).

Four concentrations of test compounds were used, i.e., 10, 5, 1, and 0.1 μM. The dead-cell population was determined by LDH enzymic activity and the results, presented in Table II, were compared with the 100% mortality based on the 500 μM glutamate treated cells without test compound protection. All compounds tested demonstrated a dose-related efficacy in decreasing cell mortality.

TABLE II

| TEST COMPOUND | CONCENTRATION | % OF DEAD |
| --- | --- | --- |
| (1S,2R) 1-[1-(2-thienyl)-2-methylcyclohexyl] piperidine | 10 | 29.7 |
| | 5 | 27.2 |
| | 1 | 32.9 |
| | 0.1 | 90.3 |
| (1S,2R) 1-[1-(2-furanyl)-2-methylcyclohexyl] piperidine | 10 | 32.1 |
| | 5 | 43.3 |
| | 1 | 83.6 |
| | 0.1 | 92.5 |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A pharmaceutical composition comprising a pharmaceutical carrier and the compound (1S,2R) 1-[1-(2-thienyl)-2-alkylcyclohexyl] piperidine or a pharmaceutically acceptable salt thereof.

2. The pharmaceutical composition of claim 1, wherein said compound is (1S,2R) 1-[1-(2-thienyl)-2-methylcyclohexyl] piperidine.

3. A pharmaceutical composition comprising a pharmaceutical carrier and the compound (1S,2R) 1-(2-furanyl)-2-alkylcyclohexyl]piperidine or a pharmaceutically acceptable salt thereof.

4. The pharmaceutical composition of claim 3, wherein said compound is (1S,2R) 1-[1-(2-furanyl)-2-methylcyclohexyl] piperidine.

5. A method of preventing neuronal death in a patient, said method comprising administering to said patient a therapeutically effective amount of a pharmaceutical composition of claim 1.

6. The method of claim 5, wherein said patient is suffering from a stroke.

7. The method of claim 5, wherein said patient is suffering from trauma of the central nervous system.

8. The method of claim 5, wherein said patient is suffering from Alzheimer's disease.

9. A method of preventing neuronal death in a patient, said method comprising administering to said patient a therapeutically effective amount of a pharmaceutical composition of claim 2.

10. The method of claim 9, wherein said patient is suffering from a stroke.

11. The method of claim 9, wherein said patient is suffering from trauma of the central nervous system.

12. The method of claim 9, wherein said patient is suffering from Alzheimer's disease.

13. A method of preventing neuronal death in a patient, said method comprising administering to said patient a therapeutically effective amount of a pharmaceutical composition of claim 3.

14. The method of claim 13, wherein said patient is suffering from a stroke.

15. The method of claim 13, wherein said patient is suffering from trauma of the central nervous system.

16. The method of claim 13, wherein said patient is suffering from Alzheimer's disease.

17. A method of preventing neuronal death in a patient, said method comprising administering to said patient a therapeutically effective amount of a pharmaceutical composition of claim 4.

18. The method of claim 17, wherein said patient is suffering from a stroke.

19. The method of claim 17, wherein said patient is suffering from trauma of the central nervous system.

20. The method of claim 17, wherein said patient is suffering from Alzheimer's disease.

* * * * *